United States Patent [19]

Kleiss

[11] 4,170,893

[45] Oct. 16, 1979

[54] SLOPING BASELINE COMPENSATION FOR A CHROMATOGRAPHIC ANALYZER

[75] Inventor: Louis D. Kleiss, Borger, Tex.

[73] Assignee: Phillips Petroleum Company, Bartlesville, Okla.

[21] Appl. No.: 862,065

[22] Filed: Dec. 19, 1977

[51] Int. Cl.² .......................................... G01N 31/08
[52] U.S. Cl. .................................................. 73/23.1
[58] Field of Search ........................ 73/23.1; 364/833

[56] References Cited

U.S. PATENT DOCUMENTS

| 3,152,301 | 10/1964 | Burk | 323/75 |
|---|---|---|---|
| 3,257,847 | 6/1966 | Levy et al. | 73/23.1 |
| 3,316,751 | 5/1967 | Burk | 73/23.1 |
| 3,381,519 | 5/1968 | Ashmead et al. | 73/23.1 |
| 3,590,628 | 7/1971 | Orr | 73/23.1 |
| 3,717,028 | 2/1973 | Annino et al. | 73/23.1 |
| 3,797,300 | 3/1974 | Sato | 73/23.1 |

Primary Examiner—Charles A. Ruehl

[57] ABSTRACT

A method and apparatus is disclosed for correcting errors in a chromatographic analysis wherein the trailing edge of a strong peak interferes with the integration of the trailing peak which follows the strong peak. In one embodiment of the invention two functions of the trailing peak are electrically integrated and summed to produce a correct peak integration. In a second embodiment of the invention the baseline is shifted and the integration of the trailing peak is performed with respect to the shifted baseline to produce a correct peak integration.

7 Claims, 7 Drawing Figures

SLOPING BASELINE COMPENSATION FOR A CHROMATOGRAPHIC ANALYZER

This invention relates to chromatography. In a particular aspect this invention relates to methods and apparatus for correcting errors in peak integration caused by interference produced by the trailing edge of a preceding large peak.

In a typical chromatographic analyzer, the detector amplifier voltage rises and falls as peaks are eluted at predictable times. An electrical integrator is programmed to operate over a time interval representing a particular peak. Just before the integration begins, the integrator reference voltage is clamped, or zeroed, at the detector amplifier voltage which exists before integration. This establishes a flat baseline against which the peak of interest is integrated. This method of zeroing, well known and widely used, serves well when the peak of interest is distinct from other peaks. However, large measurement error can occur when a small peak of interest closely follows a large peak. The trailing edge of the large peak can overlap the relatively small peak of interest. Seen on a voltage recorder, the peak of interest appears as a small hump on a downsloping baseline. When this sloping baseline is ignored, using the conventional flat baseline integration method above, a true integration of the small peak cannot be secured.

Accordingly, it is an object of this invention to provide methods and apparatus for correcting errors in peak integration caused by interference produced by the trailing edge of a preceding large peak. Another object of this invention is to provide electrical integration of a chromatographic analyzer peak signal with respect to a sloping baseline.

In accordance with the present invention an integrating circuit is utilized to integrate the detector amplifier voltage over a specified time period. The detector amplifier voltage will form a peak over the specified time period and integration of this peak with respect to the detector amplifier voltage at the beginning of the integration period gives an indication of the relative concentration of the component being analyzed by the chromatographic analyzer. If the detector amplifier voltage at the beginning of the integration period is not equal to the detector amplifier voltage at the end of the integration period, a method and apparatus is provided for correcting errors in the peak integration produced by the voltage inequalities at the beginning and end of the integration period.

In a preferred embodiment the error in the peak integration is corrected by integrating a constant voltage over the integration period. The thus integrated voltage is then multiplied by the difference between the detector amplifier voltage at the beginning of an integration period and the detector amplifier voltage at the end of the integration period. The result is then added to the peak integration to produce a correct integration of the peak of interest.

In a less preferred embodiment of the invention the error in the peak integration is corrected by shifting the integration baseline, which is the detector amplifier voltage at the beginning of the integration period, to a voltage level which is half way between the voltage level at the beginning of the integration period and the voltage level at the end of the integration period. The integration of the peak of interest is then performed with respect to the shifted baseline which will again produce a correct integration of the peak of interest.

Other objects and advantages of the invention will be apparent from the description of the invention and the appended claims thereto as well as from the detailed description of the drawings in which:

Figure 1:
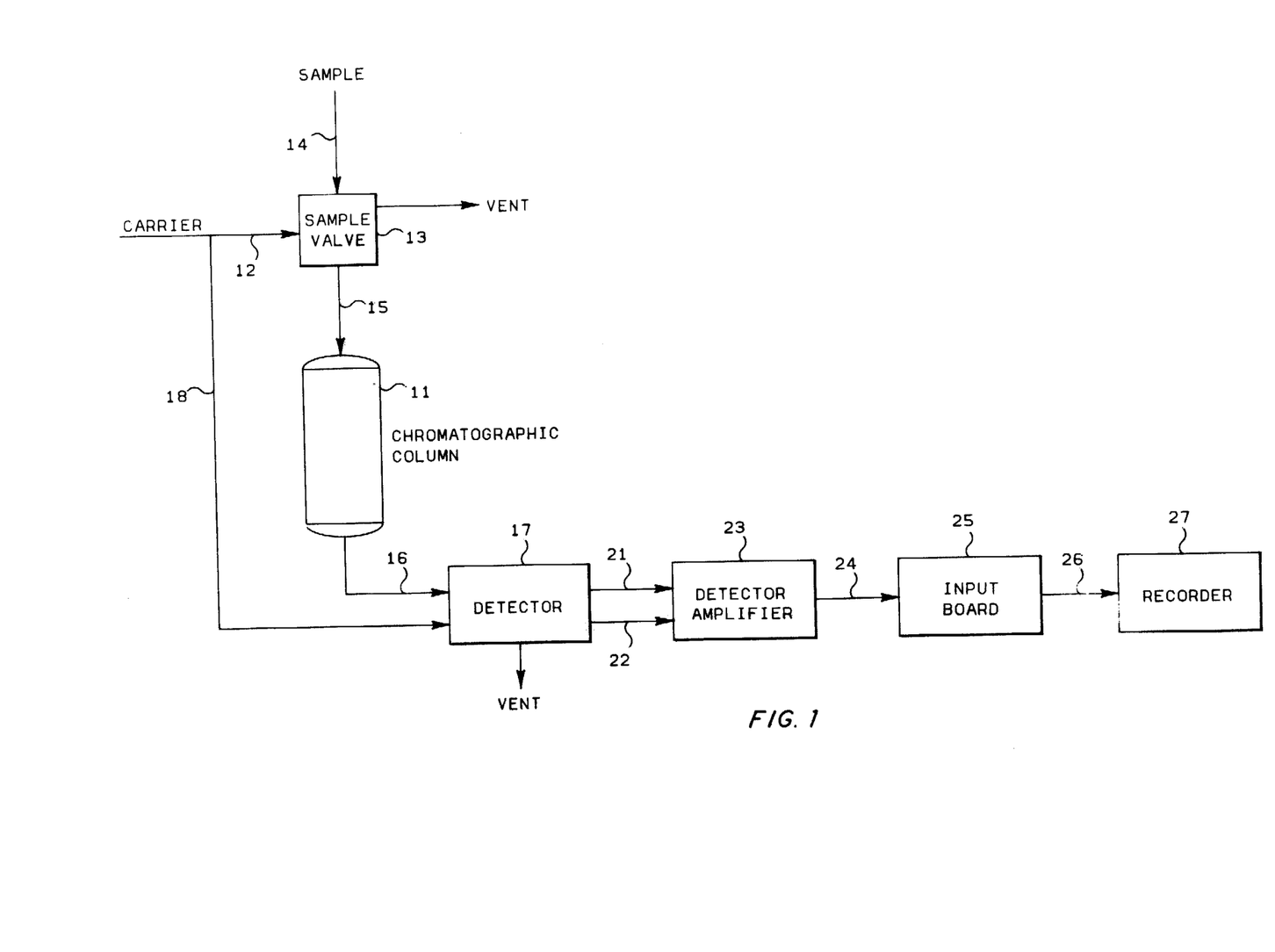
FIG. 1 is an illustration of a chromatographic analysis system.

Referring now to the drawings and in particular to FIG. 1, there is shown a chromatographic column 11. A carrier fluid is introduced through conduit means 12 into sample valve 13. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a detector means 17. Carrier fluid is passed through the reference portion of detector means 17 by being introduced into the second inlet of detector means 17 through conduit means 18 which communicates with conduit means 12. Carrier fluid also flows through sample valve 13 and chromatographic column 11 to the first inlet of detector means 17.

At the beginning of an analysis period, sample valve 13 is actuated to introduce a predetermined volume of sample into the carrier fluid flowing through chromatographic column 11. The constituents of the sample are eluted in sequence and flow from chromatographic column 11 through conduit means 16 to the sample portion of detector means 17.

Detector means 17 establishes a differential output by establishing and electrical signal 21 representative of the composition of the carrier fluid carrying the sample passing through the sample portion of detector means 17 and an electrical signal 22 representative of the composition of the carrier gas only in the reference portion of detector means 17. Signals 21 and 22 are then compared by detector amplifier 23 to produce signal 24 representative of a chromatographic analyzer output signal. Signal 24 is supplied to the input board 25. Input board 25 operates on signal 24 to produce signal 26 representative of either the peak height or the peak area of the selected components in the stream. Signal 26 is supplied to recording means 27 where it is stored.

As has been stated, an object of this invention is to reduce errors in peak integration caused by a drifting baseline introduced by the trailing edge of a preceding large peak. Circuitry on the input board 25 is utilized to achieve this object. Peak integration is also accomplished by circuitry on the input board 25.

Figure 2:
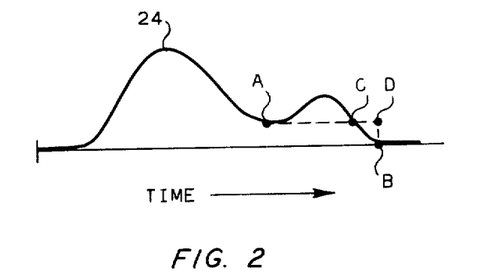
FIG. 2 is an illustration of two overlapping peaks in an exemplary output of chromatographic analysis.
Figure 3:
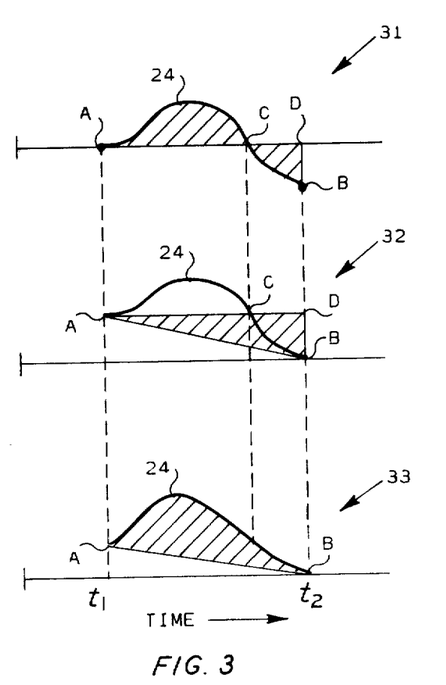
FIG. 3 is an illustration of the summation of two integrations of functions of the trailing peak of the curve of FIG. 2.

The problem addressed by this invention and preferred solution to the problem is shown in general in FIGS. 2 and 3. FIG. 2 is representative of a typical chromatographic analyzer output signal 24 which consists of a large peak followed by a smaller peak. As is shown in FIG. 2 the large peak may interfere with the smaller peak. A and B are detector amplifier output voltages at the chromatographic analyzer's gate turn-on and turn-off times, respectively. The peak area integration is commonly zeroed at voltage A. Voltage above A is integrated positively; voltage less than A is integrated negatively and subtracted from the positive portion. The line AD would represent the baseline. The area enclosed by line AC and signal 24 would be integrated positively. The area enclosed by lines CD, DB and signal 24 would be integrated negatively and subtracted from the positive portion. There would be no relationship between the integration and the actual area of the measured peak.

The present invention in a preferred embodiment calculates and adds a baseline correction to the integration described above. This is shown in FIG. 3. The part of FIG. 3 labeled 31 represents the integration carried out as described in connection with FIG. 2. The part of FIG. 3 labeled 32 represents the correction factor for the integration shown in part 31. The shaded area of part 32 is equal to $(A-B)/2$ integrated over the time t, where A and B are voltage levels as has been previously stated and where t is the length of the period of integration for the particular peak represented by $t_2 - t_1$. When the shaded area shown in part 32 of FIG. 3 is added to the integration performed as shown in part 31 the result is the shaded area shown in part 33. It can be seen that the shaded area of part 33 corresponds more closely to the area under the peak formed by the second component after excluding the effect of the trailing edge of the peak formed by the first component, than would be achieved by zeroing the second signal at voltage level A. Thus the composite integration shown in part 33 is a more accurate representation of the second peak.

Figure 4:
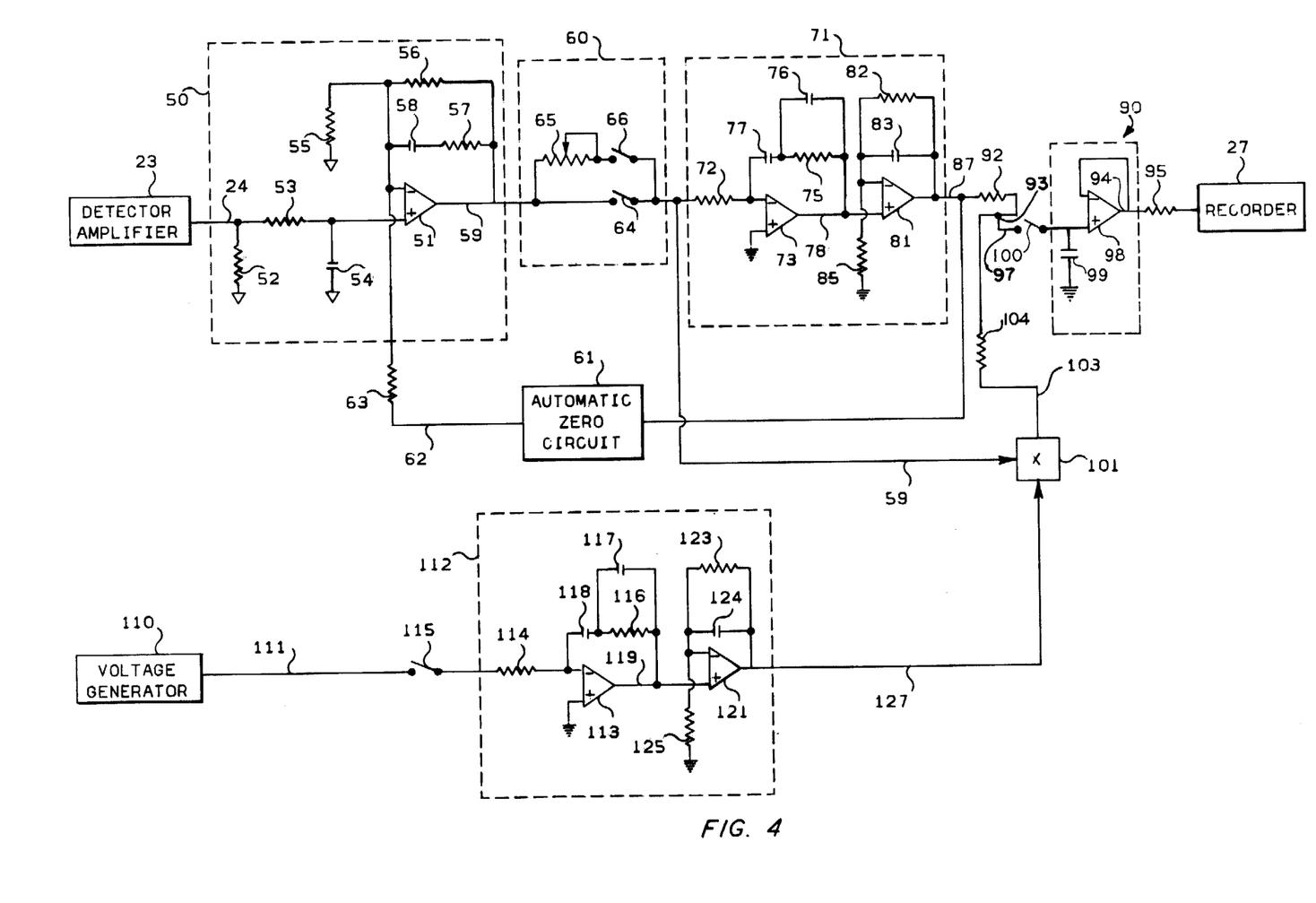
FIG. 4 is a schematic representation of an electrical circuit for accomplishing the integration and summation of FIG. 3.

FIG. 4 is a preferred embodiment of the input board shown in FIG. 1 which is capable of performing the functions shown in FIG. 3. The output signal 24 from detector amplifier 23 is first processed by the preamplifier circuit 50. Signal 24 from detector amplifier 23 is fed to the non-inverting terminal of operational amplifier 51 through a filter element made up of resistors 52 and 53 and capacitor 54. The output signal 62 from the automatic zeroing circuit 61 is fed to the inverting terminal of operational amplifier 51 through resistor 63. The feedback network for operational amplifier 51 is connected to the inverting terminal and is made up of resistors 55, 56, 57 and capacitor 58.

The attenuating circuit 60 is utilized to reduce the signal level of signal 59 if desired. The output signal 59 from operational amplifier 51 is supplied to an integrating circuit 71 directly if switching means 64 is closed or is fed to the integrating circuit 71 through a variable resistor 65 if switching means 66 is closed. Signal 59 is also supplied as one input to multiplying means 101.

Signal 59 is supplied through resistor 72 to the inverting terminal of operational amplifier 73. The non-inverting terminal of operational amplifier 73 is grounded. The feedback circuit for operational amplifier 73, made up of resistor 75 and capacitors 76 and 77, is fed to the inverting terminal of operational amplifier 73.

The output signal 78 from operational amplifier 73 is fed to the non-inverting terminal of operational amplifier 81. The feedback network for operational amplifier 81, made up of resistor 82 and capacitor 83 is fed to the inverting terminal of operational amplifier 81 and to ground through resistor 85.

The output signal 87 from operational amplifier is fed through resistor 92 to summing junction 93. Output signal 87 is also provided as an input to the automatic zeroing circuit 61.

Signal 111 represents a fixed voltage generated by voltage generator means 110. Signal 111 is supplied to the integrating circuit 112 when switching means 115 is closed. When switching means 115 is closed signal 111 is supplied to the inverting terminal of operational amplifier 113 through resistor 114. The non-inverting terminal of operational amplifier 113 is grounded. The feedback circuit for operational amplifier 113, made up of resistor 116 and capacitors 117 and 118 is supplied to the inverting terminal of operational amplifier 113.

The output signal 119 from operational amplifier 113 is supplied to the non-inverting terminal of operational amplifier 121. The feedback circuit for operational amplifier 121, made up of resistor 123 and capacitor 124, is supplied to the inverting terminal of oerational amplifier 121 and is supplied to ground through resistor 125. The output signal 127 from operational amplifier 121 is fed as a second input to multiplying means 101. Signal 103 from multiplying means 101 is fed as a second input through resistor 104 to summing junction 93. Resistors 92 and 104 comprise a summing network, and the signal 97 at summing junction 93 is proportional to the sum of signals 87 and 103.

Sample-and-hold circuit 90 is comprised of operational amplifier 98 and capacitor 99. When switching means 100 is momentarily closed, the output signal 94 of sample-and-hold circuit 90 assumes and holds the voltage of signal 97 which exists at the moment of closure. The voltage from sample-and-hold circuit 90 goes through resistor 95 to recording means 27.

At the start of an integration period, the integrating circuit 71 input is essentially at ground and the output signal 87 has a zero voltage level. Just before the integration period begins, the automatic zero circuit 61 sets the preamplifier circuit 50 output signal 59 to zero with corresponds to voltage level A in part 31 of FIG. 3. The automatic zeroing circuit 61 is well known in the art of chromatography. A typical zeroing circuit which could be utilized in the present invention is described in U.S. Pat. No. 3,152,301.

When either switching means 64 or 66 is closed the integration is started by the integrating circuit 71. At the end of the integration period the output signal 87 from the integrating circuit 71 is representative of the crosshatched area enclosed by the lines CD, DB and signal 24 shown in part 31 of FIG. 3 subtracted from the crosshatched area enclosed by the line AC and signal 24 shown in part 31 of FIG. 3.

At the start of each integration period, the output of integration circuit 112 is set to zero. A fixed voltage supplied by voltage generator 110 is integrated, simultaneously with the integraton of signal 59, by the integrating circuit 112 for the integration period. The output signal 127 from the integrating circuit 112 is thus proportional to the integration time.

Signal 127 is supplied to multiplying means 101. Multiplying means 101 is also supplied with signal 59 which will be proportional to the voltage difference between A and B shown in FIG. 3 at the end of the integration period. The fixed voltage is selected as the inverse of the multiplier 101 gain divided by two because the area of a triangle is equal to one-half the base times the height. Signals 59 and 127 are multiplied by multiplying means 101 to produce signal 103 which is representative of the triangular crosshatched area shown in part of FIG. 3. Signals 87 and 103 are then summed in the resistor network comprised by resistors 92 and 104 to create signal 97. At the end of the integration period, signal 97 represents the area under the peak formed by signal 24 as shown by the crosshatched area of part 33 of FIG. 3. Switching means 100 closes momentarily at the end of the integration period, and the sample-and-hold circuit 90 clamps signal 94 and delivers it to recording means 27 until another integration is performed on the next cycle of the analyzer.

Figure 5:
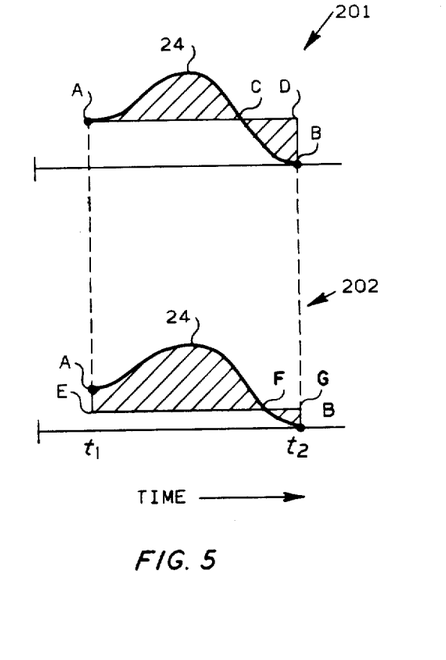
FIG. 5 is an illustration comparing a standard integration with the integration of the integration of the trailing peak of the curve of FIG. 2 in accordance with another embodiment of the invention.

A second less preferred solution to the problem of reducing errors in peak integration caused by a drifting baseline introduced by the trailing edge of a preceding large peak is illustrated in FIG. 5. Part 201 of FIG. 5 corresponds to part 31 of FIG. 3 and has been previously described. Part 202 of FIG. 5 presents a solution to the error in the actual area under the measured peak that is shown in part 201. The baseline AD shown in part 201 has been shifted in part 202. Line EFG represents the new baseline. The voltage level represented by the line EFG in part 202 is halfway between voltages A and B. In part 202 the area enclosed by the lines FG, GB and signal 24 is subtracted from the area enclosed by the lines AE, EF and signal 24. The resulting area is equal to the area under the measured peak as is shown in part 33 of FIG. 3.

Figure 6:
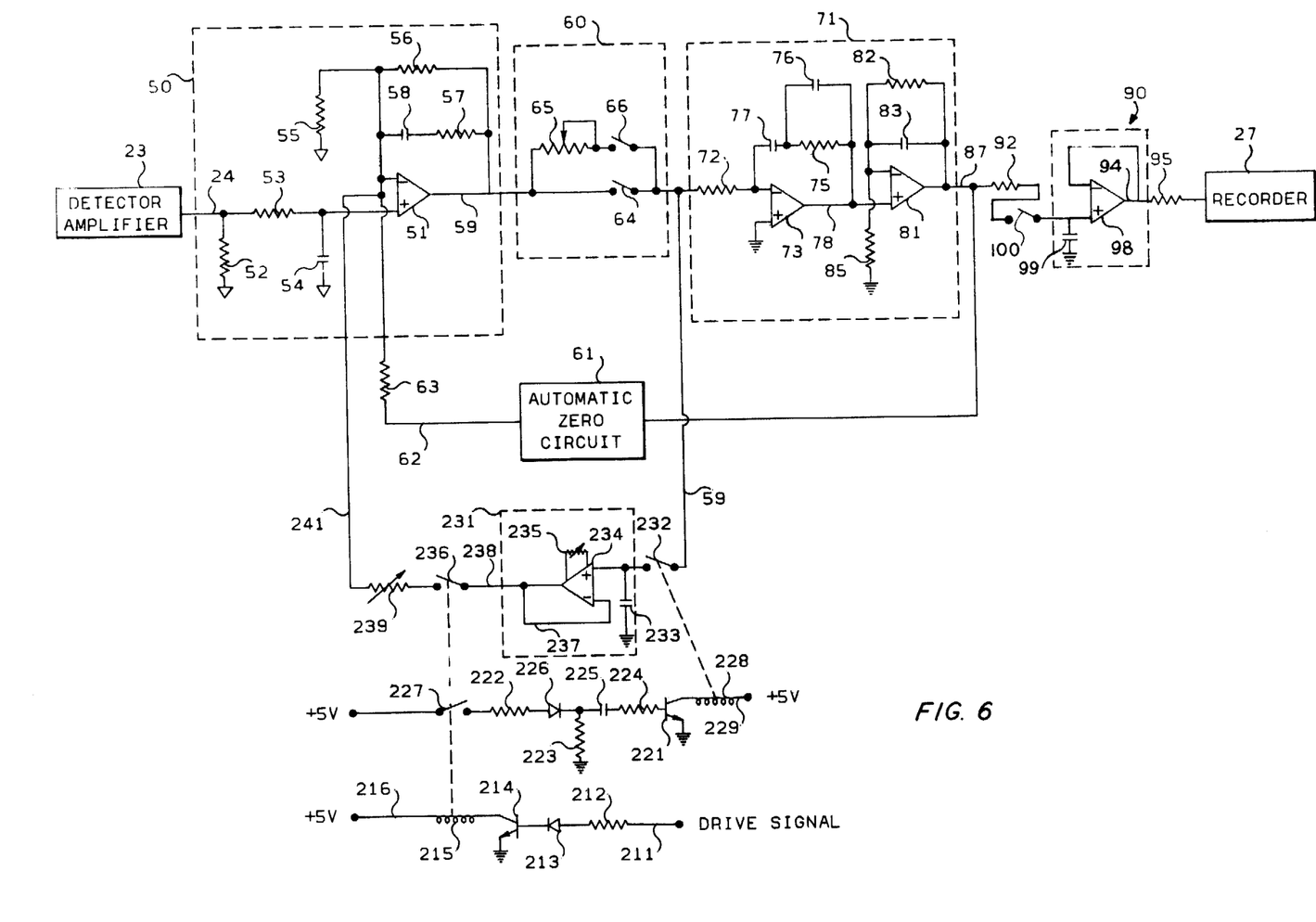
FIG. 6 is a schematic representation of an electrical circuit for accomplishing the integration shown in the lower part of FIG. 5.

FIG. 6 presents a less preferred embodiment of the input board shown in FIG. 1 which is capable of performing the baseline shift shown in part 202 of FIG. 5. It assumes that the term, (Voltage A − Voltage B)/2, is substantially constant from one integration to the next. This term is calculated and stored during each integration. During the next integration this stored term is used to bias the integrator reference voltage, thus performing the baseline shift shown in part 202 of FIG. 5. The preamplifier circuit 50, the attenuating circuit 60, the automatic zero circuit 61, the integrating circuit 71 and the sample-and-hold circuit 90 are identical to the circuits illustrated and described in conjunction with FIG. 4.

A drive signal 211 which is at a positive voltage level during an integration cycle and is at a zero or negative voltage level at the end of an integration cycle is supplied through resistor 212 and diode 213 to the base of transistor 214. The emitter of the transistor 214 is grounded. The collector of transistor 214 is connected to relay 215. Relay 215 is also connected to a +5 volt power supply shown as signal 216.

A second +5 volt power supply is supplied to the base of transistor 221 through a pulse circuit made up of resistors 222, 223, and 224; capacitor 225; and diode 226 when switching means 227 is closed. The emitter of transistor 221 is grounded. The collector of transistor 221 is connected to relay 228. Relay 228 is also supplied by a +5V power supply shown as signal 229.

Signal 59 is supplied to a sample and hold circuit 231 when switching means 232 is closed. The sample and hold circuit is made up of capacitor 233, operational amplifier 234, and a variable resistor 235. Signal 59 is fed to the non-inverting input of operational amplifier 234. The feedback loop 237 for operational amplifier 234 is connected to the inverting terminal of operational amplifier 234. The output signal 238 from operational amplifier 234 is supplied through variable resistor 239 to the inverting input of operational amplifier 51 as signal 241 when switching means 236 is closed.

At the end of an integration cycle the drive signal 211 will go to zero or to a negative voltage. This will cause transistor 214 to turn off causing relay 215 to close switching means 227. When switching means 227 is closed transistor 221 will turn on momentarily, causing relay 228 to momentarily close switching means 232. Signal 59 is momentarily supplied to the noninverting terminal of operational amplifier 234. Signal 59 will be representative of the voltage level B shown in FIG. 5 at the end of an analysis cycle. This voltage level is held in the sample and hold circuit 231.

When the next integration cycle of the peak of interest begins, the drive signal 211 will be at a positive voltage level causing transistor 214 to turn on thus causing relay 215 to close switching means 236 and open switching means 227. When switching means 236 is closed, output signal 238, which is representative of voltage level B, from the sample and hold circuit 231 will be supplied through a variable resistor means 239 to the inverting input of operational amplifier 51. The variable resistor is calibrated so as to provide an input signal 241 to the inverting input of operational amplifier 51 equivalent to that produced by a detector amplifier voltage change of (−)B/2 when applied to the noninverting terminal. Note that voltage level B is referenced from voltage level A.

Signal 241 acting in conjunction with the automatic zeroing circuit 61 acts to establish the new baseline EFG shown in part 202 of FIG. 5. The peak of interest is again integrated with respect to the new baseline which gives a correct area under the peak of interest as is shown in part 202 of FIG. 5.

Figure 7:
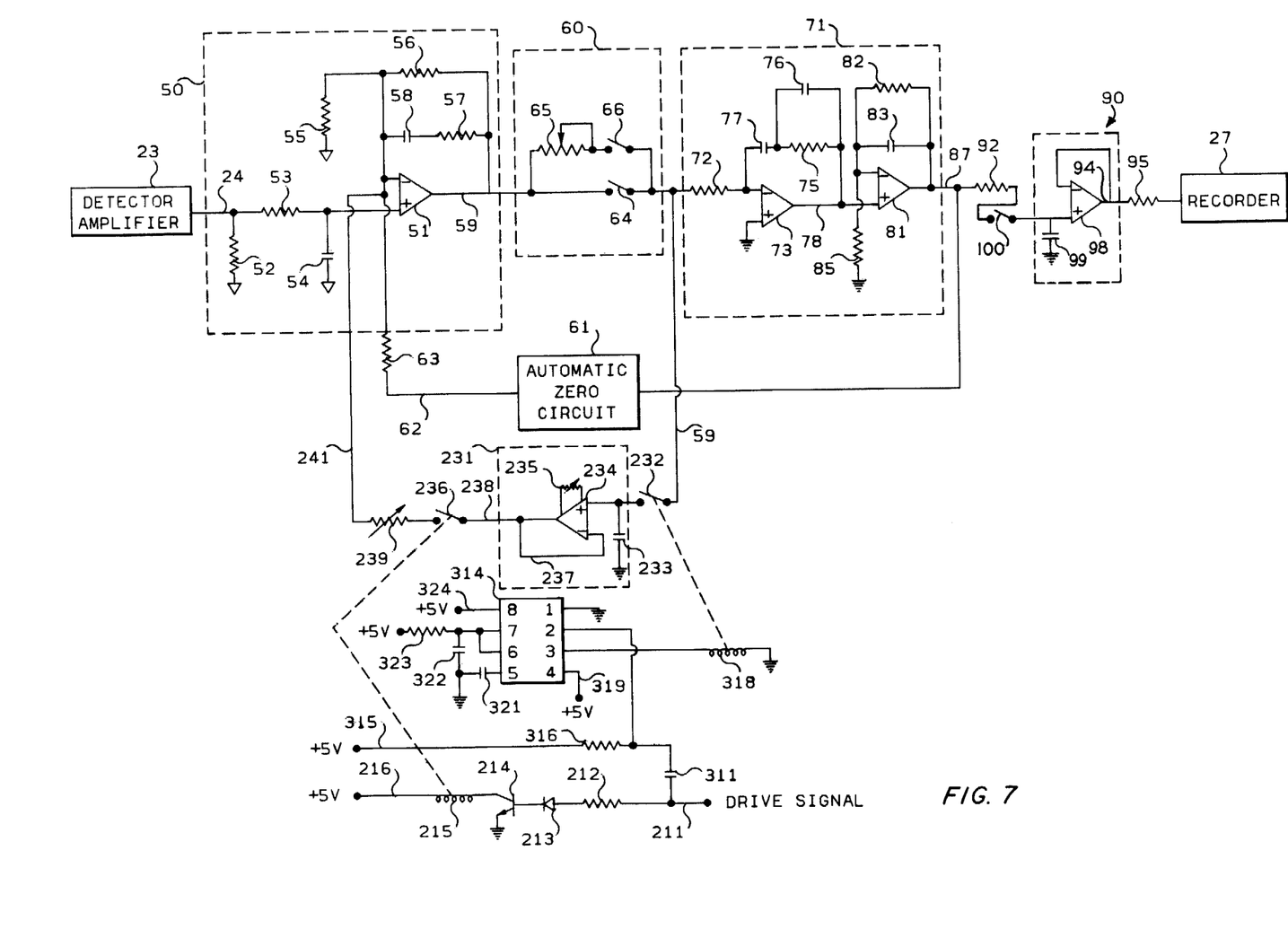
FIG. 7 is a modification of the schematic shown in FIG. 6.

FIG. 7 presents a second embodiment of the input board shown in FIG. 1 which is capable of performing the baseline shift shown in part 202 of FIG. 5. Again the preamplifier circuit 50, the attenuating circuit 60, the automatic zero circuit 61, the integrating circuit 71 and the sample-and-hold circuit 90 are identical to the circuits illustrated and described in conjunction with FIG. 4.

As was described in conjunction with FIG. 5, a drive signal 211 which is at a positive voltage level during an integration cycle and is at a zero or negative voltage level at the end of an integration cycle is supplied through resistor 212 and diode 213 to the base of transistor 214. The emitter of transistor 214 is grounded. The collector of transistor 214 is connected to relay 215. Relay 215 is also connected to a +5 volt power supply shown as signal 216.

The drive signal 211 is also supplied through capacitor 311 to the second input of a timer 314 which is a 555 timer manufactured by Signetics. A +5 volt power supply which is shown as signal 315 is also supplied to the second input of timer 314 through resistor 316. Terminal 1 of timer 314 is grounded. Terminal 3 is connected to relay 318. Terminal 4 of timer 314 is connected to a +5 volt power supply through signal 319. Terminals 5, 6, and 7 of timer 314 are interconnected as shown by capacitors 321 and 322 and resistor 323 which is connected to a +5 volt power supply. Terminal 8 of timer 314 is connected to a +5 volt power supply. Terminal 8 of timer 314 is connected to a +5 volt power supply shown as signal 324.

Signal 59 is supplied to a sample and hold circuit 231 when switching means 232 is closed. The sample and hold circuit is made up of capacitor 233, operational amplifier 234, and a variable resistor 235. Signal 59 is fed to tne non-inverting input of operational amplifier 234. The feedback loop 237 for operational amplifier 234 is connected to the inverting terminal of operational amplifier 234. The output signal 238 from operational amplifier 234 is supplied through variable resistor 239 to the inverting input of operational amplifier 51 as signal 241 when switching means 236 is closed.

At the end of an integration cycle the drive signal 211 will go to zero or to a negative voltage. This will cause timer 314 to close relay 318 for 0.33 seconds thus closing switching means 232 for 0.33 seconds. Signal 59 is then supplied to the non-inverting terminal of operational amplifier 234.

Signal 59 will be representative of the voltage level B shown in FIG. 5 at the end of an integration cycle. Capacitor 233 is charged to voltage level B and the voltage level is held in the sample and hold circuit 231.

When the next integration cycle of the peak of interest begins, the drive signal 211 will be at a positive voltage level causing transistor 214 to turn on thus causing relay 215 to close switching means 236. When switching means 236 is closed output signal 238, which is representative of voltage level B, from the sample and hold circuit 231 will be supplied through a variable resistor means 239 to the inverting input of operational amplifier 651. The variable resistor is calibrated so as to provide an input signal 241 to the inverting input of operational amplifier 51 which has the same effect on amplifier output as a detector amplifier voltage change of $(-)B/2$, where level B is referenced from voltage level A.

Signal 241 acting in conjunction with the automatic zeroing circuit 61 acts to establish the new baseline EFG shown in part 202 of FIG. 2. As has been previously described, the peak of interest is again integrated with respect to the new baseline which gives a correct area under the peak of interest as is shown in part 202 of FIG. 5.

The invention has been described in terms of its presently preferred embodiment as is shown in FIGS. 3 and 4 and a less preferred embodiment shown in FIGS. 5, 6, and 7. For the sake of convenience signals which supply power to the various chips shown in the schematics of FIGS. 4, 6 and 7 have been omitted. Voltage levels required by various chips are specified by the manufacturers and are well known to those familiar with the art.

Many different circuit configurations are possible which would perform the functions required of circuits shown in FIGS. 4, 6 and 7. These figures are illustrative of particular circuit configurations which will perform the required functions.

Specific components which are available commercially and which can be used in the practice of the invention as shown in FIGS. 4, 6 and 7 follow. Values of resistors and capacitors used in these particular circuits are also given. Again many different combinations of circuit values, particularly in the area of resistance and capacitance values, are possible.

| Resistors 52,53 | 4.99 KΩ | TRW/IRC |
|---|---|---|
| Resistors 55,75,116 | 15 KΩ | TRW/IRC |
| Resistor 56 | 7.5 KΩ | TRW/IRC |
| Resistor 57 | 220 KΩ | TRW/IRC |
| Resistor 63 | 22 KΩ | TRW/IRC |
| Resistors 72,114 | 1.8 KΩ | TRW/IRC |
| Resistors 82/123 | 820 KΩ | TRW/IRC |
| Resistors 85,125 | 8.2 KΩ | TRW/IRC |
| Resistors 92,104 | 10 KΩ | TRW/IRC |
| Resistor 95 | 2.2 KΩ | TRW/IRC |
| Resistor 212 | 560 Ω | TRW/IRC |
| Resistor 222 | 200 Ω | TRW/IRC |
| Resistor 223 | 100 KΩ | TRW/IRC |
| Resistor 224 | 1 KΩ | TRW/IRC |
| Resistor 323 | 1 Meg Ω | TRW/IRC |
| Resistor 316 | 27 KΩ | TRW/IRC |
| Potentiometer 239 | 20 KΩ | Bourns |
| Potentiometer 65,232 | 5 KΩ | Bourns |
| Capacitor 54 | 2 μf | Sprague |
| Capacitors 58,233 | 1 μf | Sprague |
| Capacitors 76,117,311 | .001 μf | Sprague |
| Capacitors 77,118,321 | .01 μf | Sprague |
| Capacitors 83,124 | .002 μf | Sprague |
| Capacitor 225 | 20 μf | Sprague |
| Capacitors 322,333,99 | .5 μf | Sprague |
| Operational Amplifier 51 | | Ma741C, Fairchild Electronics |
| Operational Amplifiers 73,113 | | 3542J, Burr Brown |
| Operational Amplifiers 81,121 | | 558, Signetics |
| Operational Amplifiers 234,98 | | Philbrook 1009 |
| Transistor 214 | | 2N3569, National Semiconductor |
| Transistor 221 | | 2N1711, National Semiconductor |
| Diodes 213,226 | | IN4024, National Semiconductor |
| Multiplying means 101 | | No.B05885 Multiuse Amp. Applied Automation, Inc. |
| Relay 215 | | CR2Z-1008 Clarereed |
| Relay 228, 100 | | W102 MX1, Magnecraft |
| Timer 314 | | Timer 555, Signetics |
| Relay 318 | | AWCB-16411 D414 Adams & Westlake |

-continued

| Switching means 227,232,236 | Quad Bilateral Switch CD4016C National Semiconductor |

While the invention has been described in terms of the presently preferred embodiments, reasonable variations and modifications are possible by those skilled in the art, within the scope of the described invention and the appended claims.

which is claimed is:

1. Apparatus comprising:
   means for producing a first analog output signal having a varying voltage in time;
   a first integrating circuit adapted to integrate said first analog output signal over a period beginning at time $t_1$ and ending at time $t_2$ and adapted to establish a first signal representative of the results of the integration of said first analog output signal;
   means for correcting said first signal if the voltage level of said first analog output signal at said time $t_1$ does not equal the level of said first analog output signal at said time $t_2$, said means for correcting said first signal comprising:
   means for establishing a second signal representative of the time period $t_1-t_2$;
   means for establishing a third signal representative of the difference between the voltage level of said first analog output signal at said time $t_1$ and the voltage level of said first analog output signal at said time $t_2$;
   means for multiplying said second signal and said third signal to produce a fourth signal; and
   means for algebraically summing said fourth signal and said first signal to produce a fifth signal representative of a corrected integration of said first analog output signal.

2. Apparatus in accordance with claim 1 wherein said means for producing said first analog output signal having a varying voltage in time comprises a chromatographic column and an associated detector amplifier adapted to establish said first analog output signal.

3. Apparatus in accordance with claim 1 wherein said means for establishing said second signal comprises:
   means for establishing a sixth signal having a specified voltage level; and
   a second integrating circuit adapted to integrate said sixth signal over said period beginning at said time $t_1$ and ending at said time $t_2$ to establish said second signal as the result of the integration.

4. Apparatus in accordance with claim 3 wherein said specified voltage level is the inverse of the gain, of said means for multiplying said second signal and said third signal, divided by 2.

5. A method for integrating a first analog output signal having a varying voltage in time comprising the steps of:
   integrating said first analog output signal over a period beginning at time $t_1$ and ending at time $t_2$ and establishing a first signal representative of the results of the integration of said first analog output signal;
   correcting said first signal if the voltage level of said first analog output signal at said time $t_1$ does not equal the voltage level of said first analog output signal at said time $t_2$, said step of correcting said first signal comprising:
   establishing a second signal representative of the time period $t_2-t_1$;
   establishing a third signal representative of the difference between the voltage level of said first analog output signal at said time $t_1$ and the voltage level of said first analog output signal at said time $t_2$;
   multiplying said second signal and said third signal to produce a fourth signal; and
   algebraically summing said fourth signal and said first signal to produce a fifth signal representative of a corrected integration of said first analog output signal.

6. A method in accordance with claim 5 wherein said step of establishing said second signal comprises:
   establishing a sixth signal having a specified voltage level; and
   integrating said sixth signal over said period beginning at said time $t_1$ and ending at said time $t_2$ to establish said second signal as the result of the integration.

7. A method in accordance with claim 6 wherein said specified voltage level is the inverse of the gain, of said means for multiplying said second signal and said third signal, divided by 2.

* * * * *